United States Patent
Schönfelder et al.

(10) Patent No.: US 11,406,292 B2
(45) Date of Patent: Aug. 9, 2022

(54) METHODS AND SYSTEMS FOR EVALUATING HEARING USING CROSS FREQUENCY SIMULTANEOUS MASKING

(71) Applicant: Mimi Hearing Technologies GmbH, Berlin (DE)

(72) Inventors: Vinzenz Schönfelder, Berlin (DE); Christoph Zobl, Berlin (DE)

(73) Assignee: Mimi Hearing Technologies GmbH, Berlin (DE)

( * ) Notice: Subject to any disclaimer, the term of this patent is extended or adjusted under 35 U.S.C. 154(b) by 295 days.

(21) Appl. No.: 16/847,472

(22) Filed: Apr. 13, 2020

(65) Prior Publication Data
US 2021/0315491 A1    Oct. 14, 2021

(51) Int. Cl.
*A61B 5/12* (2006.01)
*G10K 11/175* (2006.01)

(52) U.S. Cl.
CPC .......... *A61B 5/126* (2013.01); *G10K 11/1752* (2020.05)

(58) Field of Classification Search
CPC ............................ A61B 5/126; G10K 11/1752
USPC ........................................................ 600/559
See application file for complete search history.

(56) References Cited

U.S. PATENT DOCUMENTS 4,038,496 A * 7/1977 Feezor .................. A61B 5/121
                                                                    73/585
2020/0029158 A1   1/2020 Clark

OTHER PUBLICATIONS

Gong, Qin, et al.; An objective assessment method for frequency selectivity of the human auditory system; BioMedical Engineering OnLine; vol. 13, No. 1; Dec. 18, 2014; pp. 1-16.
Sek, Aleksander, et al.; "A Fast Method for the Determination of Psychophysical Tuning Curves: Further Refining"; Archives of ACoustics, Polish Scientific Publishers; vol. 32, No. 3; Aug. 13, 2007; pp. 707-728.

* cited by examiner

*Primary Examiner* — Paul Kim
(74) *Attorney, Agent, or Firm* — Polsinelli PC

(57) ABSTRACT

A method for conducting a cross frequency simultaneous masking (xF SM) test begins with generating a signal probe and a masker probe. The center frequencies of the signal and masker probes are separated by a fixed frequency ratio. An xF SM curve is generated by sweeping the signal and masker probes across a given frequency range, while maintaining the fixed frequency ratio between the two. While sweeping, the masker probe is maintained at a pre-determined masker amplitude or a series of pre-determined masker amplitudes. The amplitude of the signal probe is adjusted in response to a series of user inputs, which are then interpolated to generate the xF SM curve. Additionally, while sweeping, the signal probe can be maintained at one or more pre-determine amplitudes and the amplitude of the masker probe adjusted in response to user inputs, which are then interpolated to generate the xF SM curve.

19 Claims, 8 Drawing Sheets

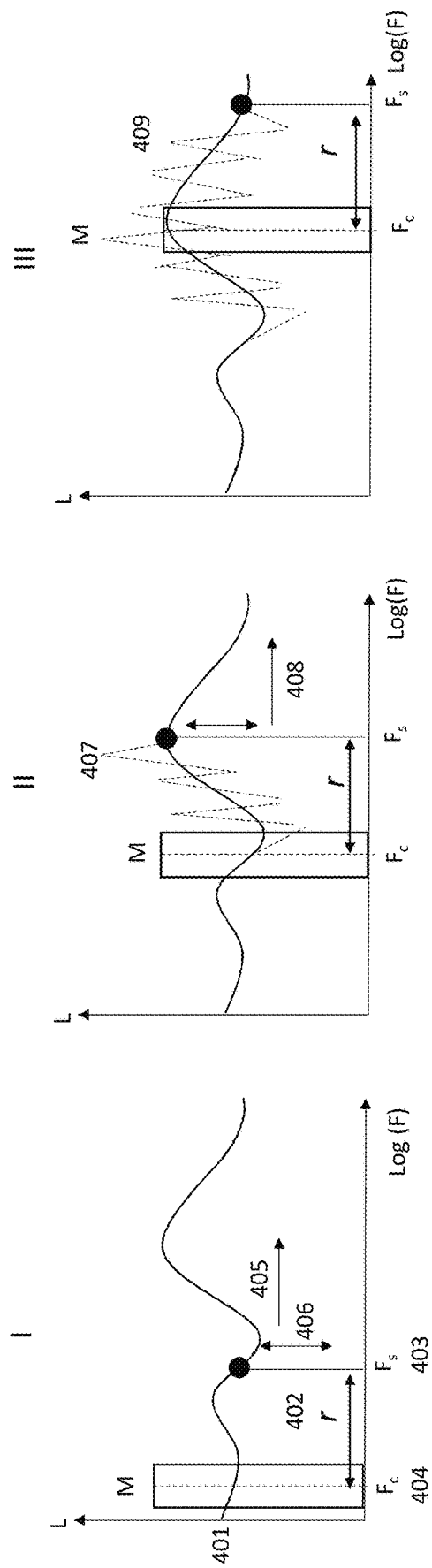

METHODS AND SYSTEMS FOR EVALUATING HEARING USING CROSS FREQUENCY SIMULTANEOUS MASKING

FIELD OF INVENTION

This invention relates generally to the field of psychophysics, audiology, audio engineering and digital signal processing (DSP), and more specifically pertains to methods and systems for evaluating hearing using cross frequency simultaneous masking.

BACKGROUND

Various behavioral methods have been developed in psychophysics to obtain psychometric data from observers, e.g., to measure a person's hearing ability. For example, conventional methods include the method of limits, the method of constant stimuli, the method of adjustment, as well as forced choice methods. In the context of measuring an observer's hearing threshold, Bekesy developed a method of "continuous adjustment" called "Bekesy tracking" [Bekesy, G. v., A new audiometer, Acta Oto-Laryngologica, 35, 41, 1-422. (1947)]. By way of a simple binary interaction of the user (pressing or releasing a single button), a parameter, i.e. the amplitude, of a sound stimulus is constantly increased or decreased resulting in an oscillation around a threshold. The threshold level can then be estimated from the points of user interaction occurring above and below the threshold.

A "sweeping" Bekesy tracking paradigm represents a variant of that general method, where a second parameter of the stimulus (e.g. frequency) is constantly changed so that the level of the perceptual threshold is traced along a range of values of that parameter of the stimulus. Originally developed for estimating pure tone auditory thresholds, the general mechanics of the Bekesy method, i.e. the continuous adjustment of parameters of a stimulus based on user interaction, have also been applied in other contexts, such as simultaneous masking suprathreshold tests, e.g. for estimating psychophysical tuning curves (PTC) and masked threshold (MT) curves. [Sek, A., Alcantara, J., Moore, B. C. J., Kluk, K., & Wicher, A., Development of a fast method for determining psychophysical tuning curves, International Journal of Audiology, 44(7), 408-420. (2005)]. Bekesy audiometry has been recognized as a useful diagnostic tool in clinical audiology [see, e.g., Granitz, D. W. "An evaluation of diagnostic parameters of Bekesy audiometry", LSU Historical Dissertation Theses 2052 (1971)].

In a Bekesy tracking/continuous adjustment paradigm, for example, a user is tasked with pressing a button when he hears a sound and releasing the button when he does not. As long as the button is pressed, the parameter, i.e. the amplitude, of the stimulus is continuously reduced until the user releases the button. When the button is released, the parameter, i.e. the amplitude, of the stimulus is increased. As a result of this procedure, the parameter of the stimulus should continuously oscillate around the threshold level of a user at a given frequency.

Owing to its intuitive and engaging character, this method of continuous user-controlled adjustment of the parameter of the stimulus lends itself particularly well for (but is not limited to) consumer (e.g. mobile device) implementations of psychometric tests, such as audiometric hearing tests. Users can quickly learn the task and are not required to directly look at the device during a test, such that the user's continuous engagement allows for a large body of data to be collected.

In the context of using a sweeping Bekesy paradigm for a simultaneous masking threshold test, the test duration can be reduced to only a few minutes per ear for a given center frequency. Although this is a relatively short time for testing at a single center frequency, it would be ideal to test a user's hearing across a range of audible frequencies to get a more comprehensive assessment of user hearing health as it pertains to simultaneous masking. However, using conventional MT or PTC Bekesy sweeping techniques, this would take an amount of time impractical for a consumer context, leading to user fatigue and inaccurate test results. For example, testing at center frequencies 500 Hz, 1 kHz, 2 kHz, 4 kHz and 6 kHz for each ear to cover a broad range of the audible spectrum could take up to half an hour. Accordingly, it is an object of the disclosure to provide systems and methods for a more rapid test encompassing a wide range of audible frequencies using a simultaneous masking paradigm.

SUMMARY OF THE INVENTION

According to an aspect of the present disclosure, provided are methods and systems for evaluating hearing using cross frequency simultaneous masking. A signal probe and a masker probe are generated, wherein a center frequency of the signal probe and a center frequency of the masker probe are separated by a first fixed frequency ratio; for a given frequency range, a first xF SM curve is generated by: sweeping the signal probe and the masker probe across the given frequency range while maintaining the first fixed frequency ratio between the signal probe and the masker probe; maintaining the masker probe at a pre-determined masker amplitude; adjusting the amplitude of the signal probe in response to a series of user inputs; and interpolating the series of user inputs to generate the first xF SM curve.

In an aspect of the disclosure, the first xF SM curve is an xF MT curve, and the method further comprises: constructing, based on the xF MT curve, one or more masked threshold curves across a range of audible frequencies, one or more psychophysical tuning curves, or a pure tone threshold audiogram.

In a further aspect of the disclosure, the method further comprises, for the given frequency range, generating a second xF SM curve by: sweeping the signal probe and the masker probe across the given frequency range while maintaining a second fixed frequency ratio between the center frequency of the signal probe and the center frequency of the masker probe; adjusting the amplitude of the signal probe in response to a second series of user inputs; and interpolating the second series of user inputs to generate the second xF SM curve.

In a further aspect of the disclosure, the second fixed frequency ratio is different than the first fixed frequency ratio.

In a further aspect of the disclosure, the method further comprises interpolating between the first xF SM curve, generated for the first fixed frequency ratio, and the second xF SM curve, generated for the second fixed frequency ratio; and based on the interpolation, constructing one or more masked threshold curves across a range of audible frequencies, one or more psychophysical tuning curves, or a pure tone threshold audiogram.

In a further aspect of the disclosure, the second fixed frequency ratio is the same as the first fixed frequency ratio and the method further comprising: averaging the first xF SM curve and the second xF SM curve to generate a first averaged xF SM curve for the first fixed frequency ratio.

In a further aspect of the disclosure, the method further comprises, for the given frequency range, generating a second averaged xF SM curve for a fixed frequency ratio different than the first fixed frequency ratio; interpolating between the first averaged xF SM curve and the second averaged xF SM curve; and based on the interpolation, constructing a masked threshold curve, a psychophysical tuning curve, or an audiogram.

In a further aspect of the disclosure, the method further comprises performing a threshold hearing test or receiving user input to estimate the pre-determined masker amplitudes of the masker probe, wherein the masker is audible to a given listener of the xF SM test.

In a further aspect of the disclosure, adjusting the amplitude of the signal probe in response to the user input comprises: increasing the amplitude of the signal probe in response to a determination that the user input is received; and decreasing the amplitude of the signal probe in response to a determination that the user input is not received.

In a further aspect of the disclosure, the amplitude of the signal probe is continuously adjusted in response to the series of user inputs.

In a further aspect of the disclosure, the method further comprises providing the sweeping signal probe and masker probe to a user of an audio output device as an auditory stimulus, wherein the series of user inputs comprises user responses indicating the user's perception of the auditory stimulus.

In a further aspect of the disclosure, the user input comprises user responses obtained in response to a Bekesy testing paradigm.

In a further aspect of the disclosure, the given frequency range comprises at least a portion of the audible spectrum.

In a further aspect of the disclosure, the given frequency range is from 500 Hertz (Hz) to 6 kilohertz (kHz).

In a further aspect of the disclosure, the cross frequency simultaneous masking test is a cross frequency masked threshold test; the signal probe is a tone signal; and the masker probe is a noise signal.

In a further aspect of the disclosure, the cross frequency simultaneous masking test is a cross frequency psychophysical tuning test; the signal probe is a masking signal; and the masker probe is a tone signal.

In a further aspect of the disclosure, the first fixed frequency ratio is between 1.0 and 1.5.

In a further aspect of the disclosure, the first fixed frequency ratio is between 1.0 and 1.5; and the second fixed frequency ratio is different from the first fixed frequency ratio.

In a further aspect of the disclosure, the cross frequency simultaneous masking curve is used to calculate one or more parameters for a processing function.

In a further aspect of the disclosure, sweeping the signal probe and the masker probe across the given frequency range comprises: sweeping from an intermediate frequency value to a maximum frequency value, the maximum frequency value greater than the intermediate frequency value; sweeping from the maximum frequency value to a minimum frequency value, the minimum frequency value less than the maximum frequency value and less than the intermediate frequency value; and sweeping from the minimum frequency value to the intermediate frequency value.

Unless otherwise defined, all technical terms used herein have the same meaning as commonly understood by one of ordinary skill in the art to which this technology belongs.

The term "hearing test", as used herein, is any test that evaluates a user's hearing health, more specifically a hearing test administered using any transducer that outputs a sound wave.

The term "simultaneous masking", as used herein, is a property of the human auditory system where some sounds become inaudible in the presence of other sounds (i.e. maskers).

The term "simultaneous masking test", as used herein, is any test in which a masker probe is played simultaneously with a signal probe in order to test hearing ability. This may, for example, take the form of a psychophysical tuning curve (PTC), a masked threshold (MT) curve, or a cross frequency simultaneous masking test (xF SM).

The terms "xF MT test" and "xF MT curve", as used herein, are subsets of the terms "xF SM test" and "xF SM curve", respectively.

The term "hearing thresholds", as used herein, is the minimum sound level of a pure tone that an individual can hear with no other sound present. This is also known as the 'absolute threshold' of hearing. Individuals with sensorineural hearing impairment typically display elevated hearing thresholds relative to normal hearing individuals. Absolute thresholds are typically displayed in the form of an audiogram.

The term "headphone", as used herein, is any earpiece bearing a transducer that outputs sound waves into the ear. The headphone may be a wireless hearable, a corded or wireless headphone, a hearable device, or any pair of earbuds.

The term "sound personalization algorithm", as used herein, is defined as any digital signal processing (DSP) algorithm that processes an audio signal to enhance the audibility or clarity of the signal to a listener, or otherwise provides specific benefits to an individual listener, e.g. by matching individual sound preference(s). The DSP algorithm may be, for example: an equalizer, an audio processing function that works on the sub-band level of an audio signal, a multi-band compressive system, or a non-linear audio processing algorithm.

The term "audio output device", as used herein, is defined as any device that outputs audio, including, but not limited to: mobile phones, computers, televisions, hearing aids, headphones, smart speakers, hearables, and/or speaker systems.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understand that these drawings depict only exemplary embodiments of the disclosure and are not therefore to be considered to be limiting of its scope, the principles herein are described and explained with additional specificity and detail through the use of the accompanying drawings in which:

FIGS. 4A-C illustrate an example of a cross frequency simultaneous masking (xF SM) paradigm for an MT test, which is a subset of an xF SM test;

DETAILED DESCRIPTION

Figure 1A:
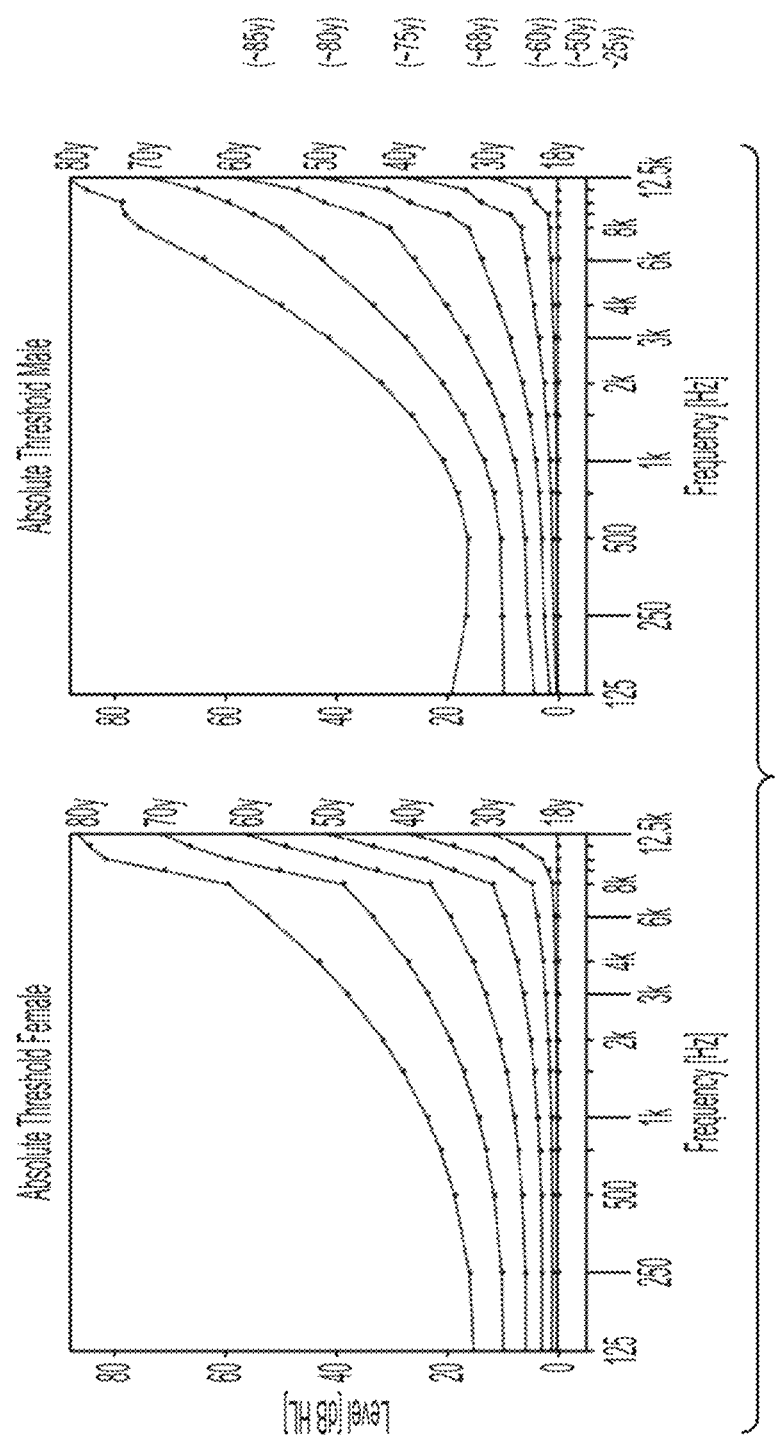
FIG. 1A illustrates the deterioration of hearing thresholds with age.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting the scope of the embodiments described herein. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

The present invention relates to creating hearing test methods that are more rapid and encompass a broader range of audible frequencies relative to traditional simultaneous masking tests, such as a psychophysical tuning curve (PTC) or a masked threshold (MT) test.

Masking is a phenomenon that occurs across all sensory modalities where one stimulus component prevents detection of another. The effects of masking are present in the typical day-to-day hearing experience as individuals are rarely in a situation of complete silence with just a single relevant signal occupying the sonic environment. The basilar membrane running along the center of the cochlea, which holds the structures responsible for neural encoding of mechanical vibrations, is frequency selective. To this extent, the basilar membrane acts to spectrally decompose incoming sonic information whereby energy concentrated in different frequency regions is represented to the brain along different auditory fibers. It can be modeled as a filter bank with near logarithmic spacing of filter bands. This allows a listener to extract information from one frequency band, even if there is strong simultaneous energy occurring in a remote frequency region. For example, an individual will be able to hear both the low-frequency rumble of a car approaching whilst listening to someone speak at a higher frequency. As relates to spectral masking, relatively high energy maskers are required to mask signals when the masker and signal have different frequency content, but relatively low intensity maskers can mask signals when their frequency content is similar.

Figure 2B:
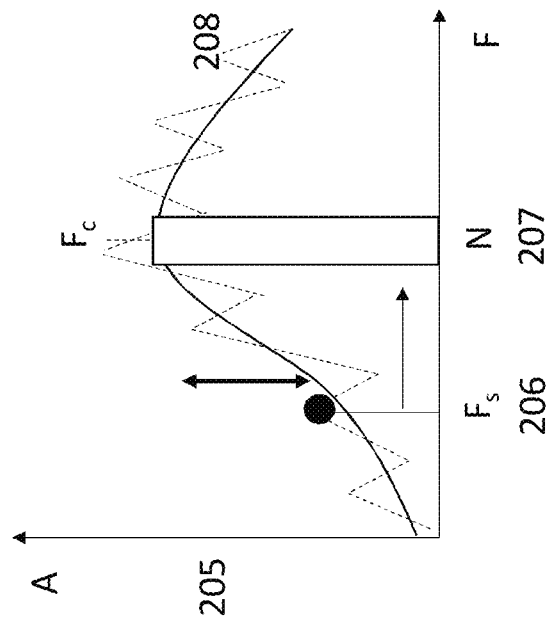
FIGS. 2A-B illustrate constructed PTC and MT curves using Bekesy tracking.
Figure 2A:
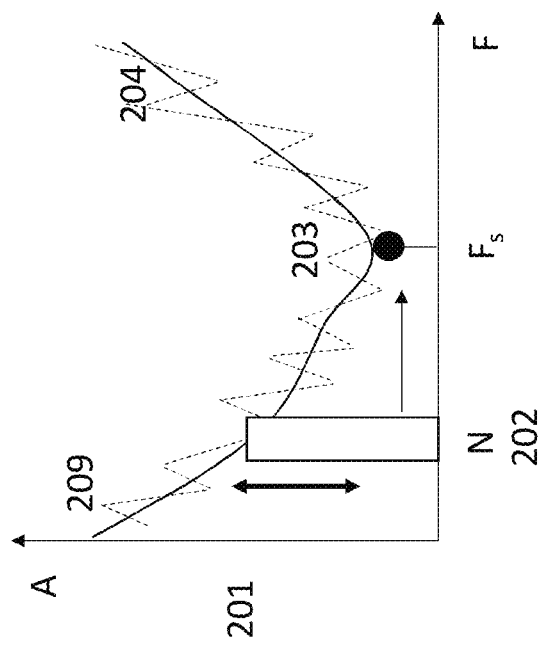

The ability of the auditory system to separate signals that differ in frequency can be described using the concept of the auditory filter that acts similarly to a spectral filter in signal processing. The characteristics of auditory filters can be measured, for example, by playing a continuous tone at the center frequency of the filter of interest, and then measuring the masker intensity required to render the probe tone inaudible as a function of relative frequency difference between masker and probe components. The resulting psychophysical tuning curve (PTC), consisting of a frequency selectivity contour extracted via behavioral testing, provides useful data to determine an individual's masking contours. For example, turning now to FIGS. 2A and 2B, in one embodiment of the test, a masking band of noise 202 is gradually swept across frequency, from below the probe frequency 203 to above the probe frequency. The user then responds when they can hear the probe and stops responding when they no longer hear the probe. This gives a jagged trace 205 that can then be interpolated to estimate the underlying characteristics of the auditory filter. Other methodologies known in the prior art may be employed to attain user masking contour curves. For instance, an inverse paradigm may be used in which a probe tone 206 is swept across frequency while a masking band of noise is fixed at a center frequency 207 (known as a "masked threshold test" or "MT test").

Figure 1B:
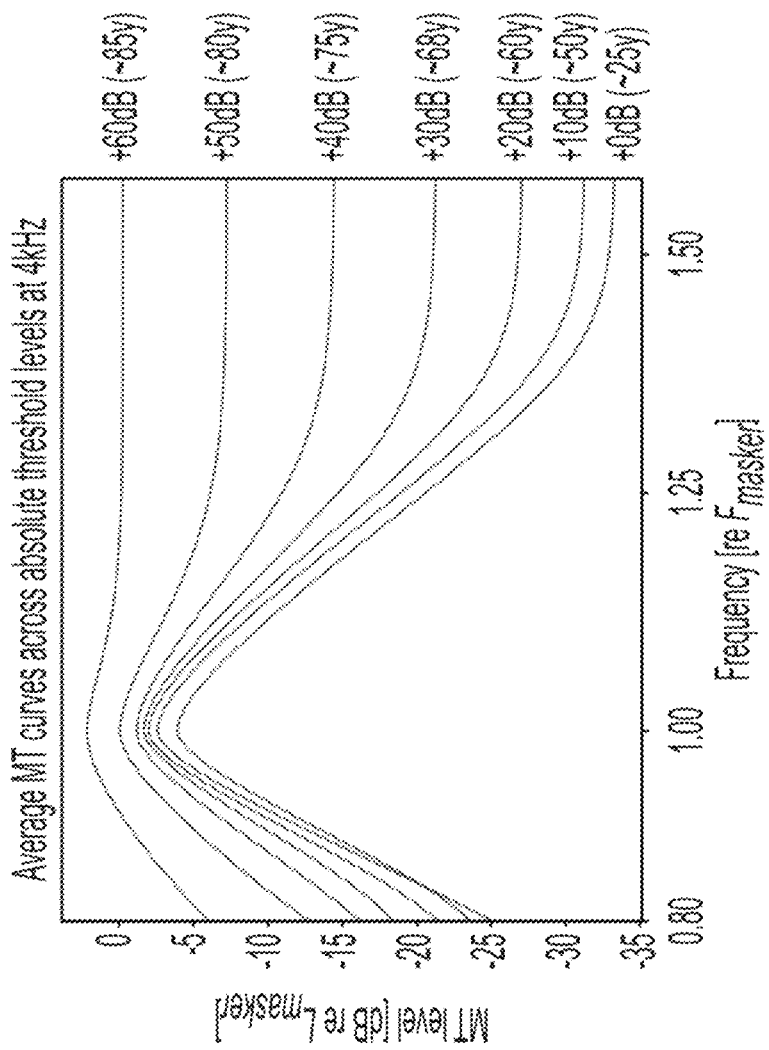
FIG. 1B illustrates masked threshold curve age trends.

Patterns begin to emerge when testing listeners with different hearing capabilities using the PTC test. Hearing impaired listeners have broader PTC curves, meaning maskers at remote frequencies more strongly impact the audibility of the probe tone. To this extent, each auditory nerve fiber of the HI listener, compared to a normal hearing person, contains information from more distant neighboring frequency bands, resulting in increasing off-frequency masking. When MT curves are segmented by listener age, which is highly correlated with hearing loss as defined by pure tone threshold (PTT) data (FIG. 1A), there is a clear trend of the broadening of MT curves with age, FIG. 1B.

Figure 3:
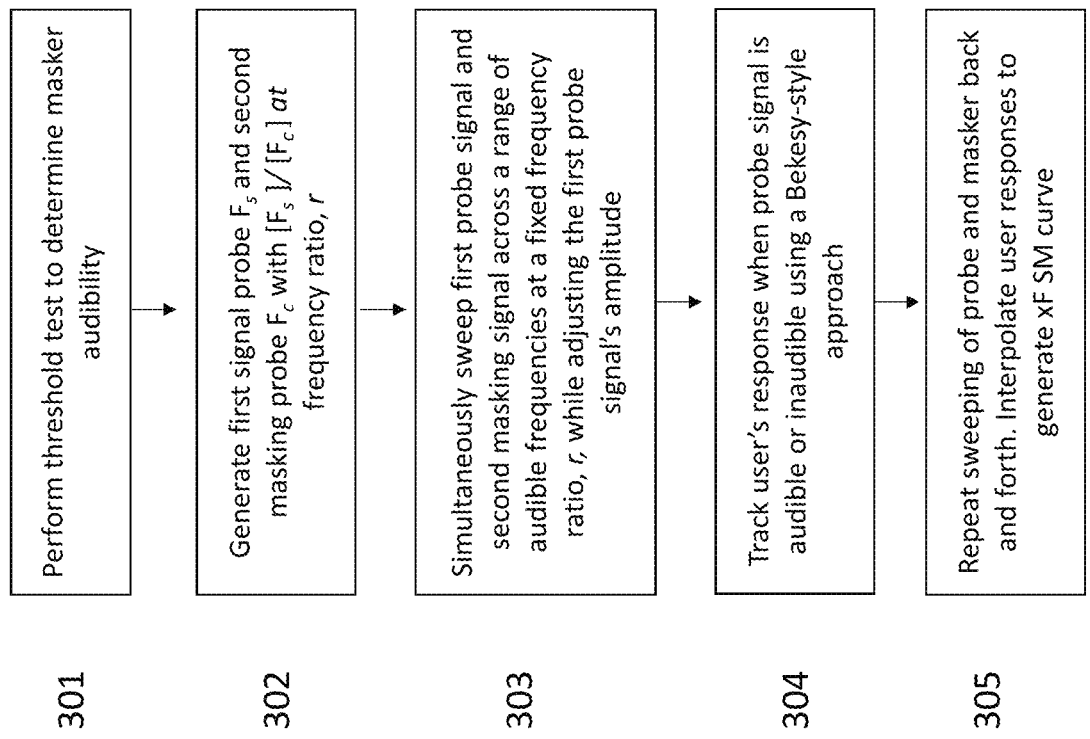
FIG. 3 illustrates an exemplary flowchart for conducting a cross frequency (xF) simultaneous masking (SM) test.

However, although these simultaneous masking tests, administered in approximately two minutes, provide rich hearing data in terms of auditory masking—they only cover a limited frequency span. To cover the typical audible spectrum for both ears, multiple tests within different frequencies ranges would have to be performed which takes up to thirty minutes, an amount of time that would be impractical due to user hearing fatigue. This then leads to inaccurate results. An analysis of MT curves as segmented by ages, and by extension, hearing capacity, yields an interesting observation: the slope of the downward segment of the MT curve, between [re F masker] values 1.0-1.5, has a significant correlation with hearing health. In some use cases, only specific aspects of the shape of the masked threshold curve, such as the slope, are of interest, rather than the more general shape in its entirety. It may possible to design a new hearing test paradigm that exploits this fact and records only that data which relates to these specific aspects of interest. By reducing the amount of data collected in each frequency region in this way, it may also be possible for the paradigm to continuously collect data on auditory masking across the auditory spectrum A new, faster and more comprehensive approach is illustrated in the flow chart in FIG. 3, denominated as a cross-frequency simultaneous masking (xF SM) paradigm. Generally, a threshold test, or an amplitude adjustment by the user, may first be performed to determine masker audibility levels, 301. Masker audibility levels 301 can include multiple different masker audibility levels for the user, e.g. measuring across multiple points of the audible spectrum.

Subsequently, once a proper masker amplitude is determined, a signal probe and a masker probe are kept at a fixed frequency ratio $(F_s/F_c)=r$ (labeled at 302), while the probes are swept 303 across the audible spectrum, F (or across some other range of audible frequencies, e.g. from 500 Hertz (Hz) to 6 kilohertz (kHz)). The amplitude of the masker probe is determined based on the masker amplitudes from 301, e.g. it may remain constant during the entirety of the test or be modified following a specific rule, e.g. dependent on masker frequency. The amplitude of the signal probe is varied in response to one or more inputs received from the user. For example, in a Bekesy paradigm, a user presses and holds a button (or provides some other user response) as long as the signal probe is audible to the user. In response to receiving this user input, the amplitude of the signal probe is decreased. When the user releases the button (or ceases to provide the some other user response), indicating that the signal probe is no longer audible to the user, then the amplitude of the signal probe is increased. In this context, a lack of a button press (or a cessation of receipt of the user response) is a user input in the same way as a button press (or receipt of user response) is a user input. In some embodiments, the rate at which the probe tone's amplitude is either increased or decreased can be on the order of ±5 dB/sec. Thus, the probe tone level is varied/adjusted in a linear fashion. In some embodiments, it is contemplated that the rate of change in probe tone amplitude is independent of the different fixed frequency ratios r that may be utilized.

At the beginning of the xF SM test disclosed herein (i.e. when the signal probe and masker probe are initially generated, prior to beginning the user data collection and frequency sweeping), the probe tone may typically be generated at some fixed level relative to that of the masker tone. For example, the probe tone can be generated 15 dB below the masker tone, although other offset values may be employed without departing from the scope of the present disclosure. In some embodiments, if the masker tone is determined in step 301 to be at or near an audibility threshold level for the user or listener performing the test, this offset arrangement might be expected to result in the xF SM test beginning with the signal probe being inaudible to the user—that is, below their auditory threshold. In some embodiments, the initial amplitude offset between the signal probe and the masker probe can depend in part on the fixed frequency ratio r that will be employed for the frequency sweeping of the xF SM test, such that the initial amplitude offset value results in a probe tone that is both likely audible to an average listener but also not too far from the perceptual threshold—which generally depends on the choice of the ratio r.

As will be explained in greater depth below, the ratio r in some embodiments is between 1.0-1.5, although other ratio values are possible. In general, the ratio r can be determined by beginning from classic MT curves, which provide a meaningful range of ratios that can then be further limited, e.g. through an iterative and/or experimental process. Based on data of MT tests that cover the full MT curve at a single masker frequency, specific points can be identified that best correlate with other hearing measures as they relate to individual users. For example, auditory thresholds across frequency are one hearing measure that may be of particular utility in identifying these correlation points.

At 304, whilst being swept at the fixed frequency ratio r, a Bekesy-style approach is used to track the user's response to the stimuli provided by the swept probe tones—with the signal probe having a variable amplitude, dependent on user interaction, and the masker probe kept at a predetermined amplitude. The frequency sweeping may then be repeated back and forth one or more times at 305, allowing for the user response(s) to be interpolated in generating an xF SM curve for the user.

In some embodiments, the frequency sweeping described herein can be performed with a variable rate of change in frequency. For example, consider a scenario in which frequency is swept from 500 Hz (lower bound) to 6 kHz (upper bound). In some embodiments, the xF SM test (and hence, the frequency sweeping process) may begin at an intermediate frequency value, e.g. a 2 kHz masker center frequency and an r*2 kHz signal frequency. From this intermediate frequency value, and while maintaining the fixed frequency ratio r, the masker tone and signal tone are swept up (i.e. frequency increased) until the masker tone reaches the maximum value given by the 6 kHz upper bound. While approaching the upper bound (or after reaching the upper bound), the rate of frequency increase slows until reaching zero, at which point frequency decrease begins. From the upper bound, frequency is then swept down (decreased) until the masker tone reaches the minimum value given by the 500 Hz lower bound. While approaching the lower bound (or after reaching the lower bound), the rate of frequency decrease slows until reaching zero, at which point frequency is increased again until the masker tone reaches the initial intermediate value of 2 kHz. In some embodiments, the above described frequency sweeping process may be performed over the course of approximately 3 minutes per ear, per xF SM test—well below the 30 minutes required by conventional MT hearing tests, as discussed previously. Note that in some embodiments, frequency may change more rapidly than in the above described example, in which case the amplitude of the signal tone is varied more rapidly.

Although the description above references a scenario in which a single ratio r is used for the fixed frequency ratio between the signal probe and the masker probe, in some embodiments it is possible that multiple of the disclosed xF SM tests can be performed with different values for ratio r. For example, multiple tests can be run for a given user, where each test has a different ratio r, e.g., r=1 for the first xF SM test, r=1.25 for the second xF SM test, and r=1.5 for the third xF SM test. For each xF SM test (or more generally, for each different ratio value r that is used across the plurality of xF SM tests), a corresponding xF SM curve can be generated. The plurality of xF SM curves generated for different values of fixed frequency ratio r between the signal probe and the masker probe can then be used to re-construct classic MT curves with a greater degree of confidence, accuracy and/or resolution than when using only a single xF SM curve for the classic MT curve reconstruction process.

Turning next to FIGS. 4A-C, a sequence depicting an example xF SM test is illustrated. The y-axis represents the amplitude of the depicted signals, which include a noise masker probe M 404 and a tone signal probe 403. The x-axis is logarithmic in frequency F. As illustrated, noise masker probe M 404 has a center frequency $F_c$ and is kept at predetermined amplitudes while being swept in frequency (i.e. the left to right progression seen in the graphs of FIGS. 4A-C). In some embodiments, the absolute width of the masker probe M 404 is dynamic, e.g. 0.2 octaves on either side of the center frequency $F_c$. Tone signal probe 403 has a frequency $F_s$ and a variable amplitude, i.e., an amplitude that is varied or adjusted while tone signal probe 403 is being swept in frequency, with an example variability or range of variability illustrated via arrow 406. In some embodiments, the rate of variation of amplitude of tone signal probe 403 is independent of the rate at which the masker probe 404 and tone signal probe 403 are frequency swept, although in other embodiments a relationship is contemplated, as will be explained in greater depth below. While performing frequency sweeping of the tone signal probe 403 and the masker probe 404, a fixed frequency ratio r is maintained, indicated in FIGS. 4A-C at 402. In some embodiments, the fixed frequency ratio r is given by $[F_s/F_c]$ where 1.0<r<1.5, although other ratio values, including values below 1.0, may be utilized without departing from the scope of the present disclosure. As illustrated, masker probe 404 and signal probe 403 are then swept 405, 408 simultaneously to higher frequencies while Bekesy-style user responses 407, 409 are recorded and then interpolated to generate curve 401.

A similar, albeit converse, approach may be used for a PTC test. In this instance, the signal tone probe at frequency $F_s$ is kept at predetermined amplitudes while the noise masker probe M, at frequency $F_m$, has a user interaction-dependent, variable amplitude. Ratio $r=[F_s/F_m]$ is kept at a similar fixed value, e.g., between 1.0<r<1.5. In some embodiments, the signal tone probe is kept above the masker probe in frequency, and the user controls the masker level (as opposed to the xF SM test, in which the user controls the signal level).

Figures 5A, 5B:
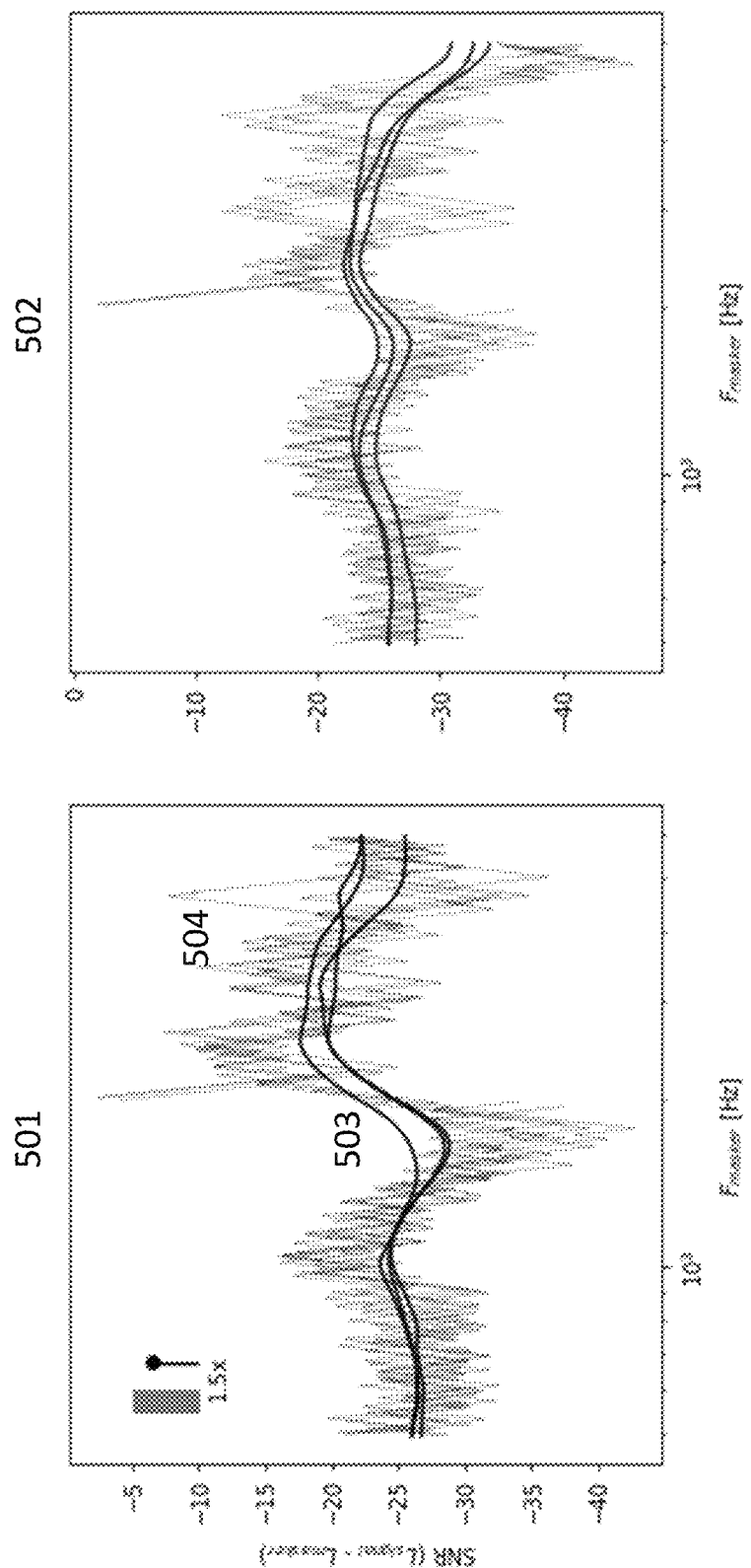
FIGS. 5A-B illustrate exemplary Bekesy testing data of an xF SM test using a noise probe to signal probe frequency ratio of 1.5.
Figure 6A:
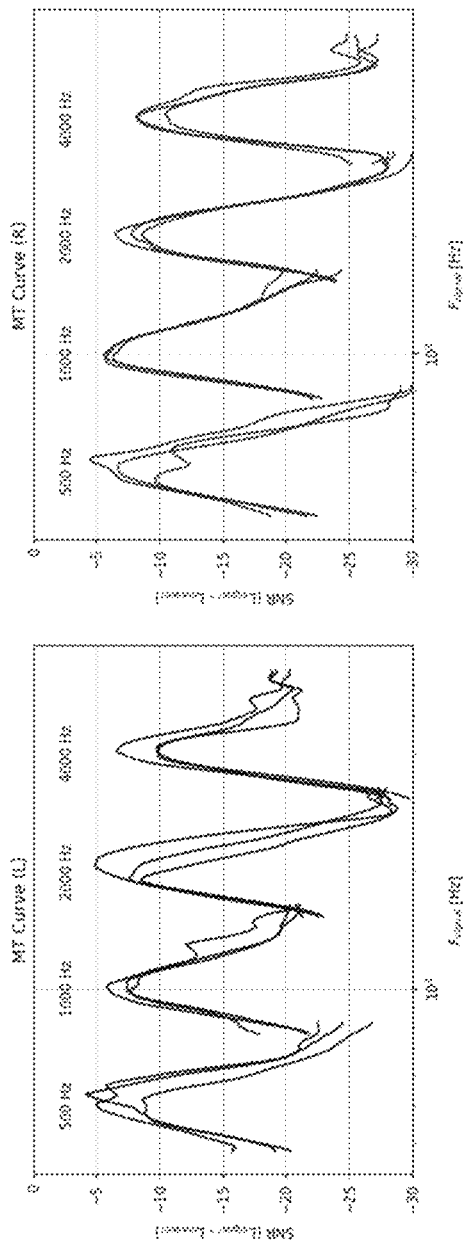
FIGS. 6A-B illustrates three sets of exemplary testing data, comparing conventional MT testing data in the left and right ears across a range of frequencies (depicted in FIG. 6A) with xF SM testing data in the left and right ears in the same frequency range using noise to signal probe frequency ratios of 1, 1.25 and 1.5 (depicted in FIG. 6B)
Figure 6B:
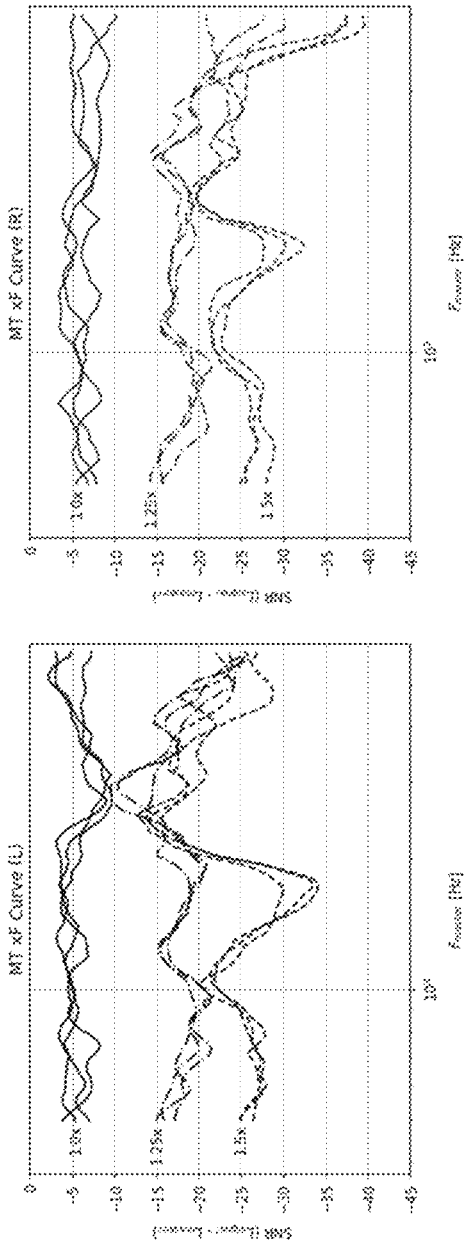
Figure 7B:
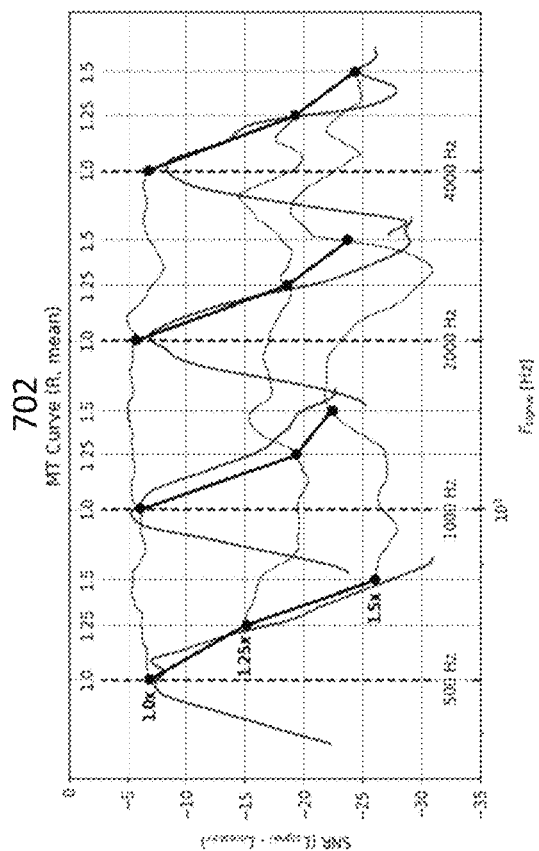
FIGS. 7A-B illustrate a juxtaposition of MT testing data with xF SM data.
Figure 7A:
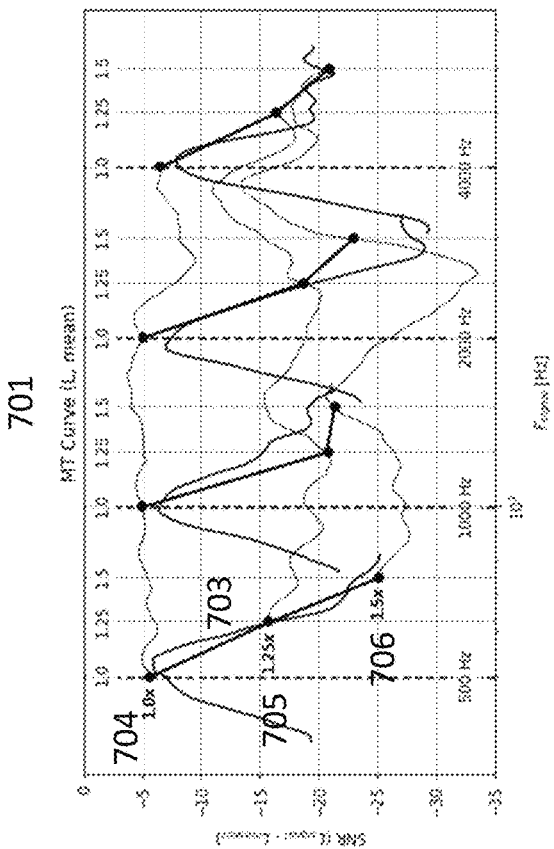

In either test, the user then responds when they can hear the probe and stops responding when they no longer hear the probe. This gives a jagged trace 504 that can then be interpolated to estimate the xF SM curve 503, as illustrated in FIGS. 5A-B. Moreover, the signal and masker probes, fixed apart at frequency ratio r, can be swept back and forth (e.g. 305 of FIG. 3) across the audible spectrum to collect more data points. Significantly, the interpolated xF SM curves strongly match the result of classic MT curves (FIGS. 6A-7B). FIG. 6A illustrates MT tests conducted three times in the left and right ears at center frequencies 500 Hz, 1 kHz, 2 kHz and 4 kHz. FIG. 6B depicts three separate xF SM tests conducted in the left and right ears, illustrated at $r=F_s/F_c$ ratios of 1, 1.25 and 1.5. When each of the curves for each respective test are averaged and then juxtaposed (as illustrated in FIGS. 7A-B), a strong relationship is observed in the mapping of xF SM curves at 1.0x (704), 1.25x (705) and 1.5x (706) ratios with the respective positions of each MT curve.

As described in commonly owned U.S. application Ser. No. 16/080,785 ("Method for accurately estimating a pure tone threshold using an unreferenced audio system"), an xF SM curve may be used to determine an audiogram of the individual—in this instance by converting the xF SM curve into a collection of MT curve or PTC across the audible spectrum (see FIGS. 7A-B). Due to the strong correlation of MT/PTC curves with pure tone threshold results, an estimate of the audiogram may be readily derived.

Following the acquirement of hearing test data from the xF SM test, the results may also be used to determine parameters for a processing function. Parameters may be calculated directly from a user's hearing data or indirectly based on preexisting entries in a database.

Briefly, DSP parameters may be calculated indirectly based on preexisting entries or anchor points in a server database (see commonly owned U.S. application Ser. No. 16/540,345, "Systems and methods for providing personalized audio replay on a plurality of consumer devices"). An anchor point comprises a typical hearing profile constructed of demographic information, such as age and sex—in which DSP parameter sets are calculated and stored on the server to serve as reference markers. Indirect calculation of DSP parameter sets bypasses direct parameter sets calculation by finding the closest matching hearing profile(s) and importing (or interpolating) those values for the user. For instance, a root mean square difference calculation, a Euclidean distance calculation (or other statistical techniques commonly known in the art) may be employed to find the closest matching xF SM curve for a user compared to an entry in a database—and the DSP parameters values associated with the closest matching curve may then be used for the user.

DSP parameters may also be calculated directly. This may be done using a hearing aid gain table prescriptive formulas. In another embodiment, ratio and threshold values for a compressor, as well as gain, in a given multiband dynamic processor signal subband may be calculated by comparing user threshold and suprathreshold information for a listener with that of a normal hearing individual, i.e. reference audiograms and PTC/MT curves (see commonly owned U.S. Pat. No. 10,398,360, "Method to Enhance Audio Signal from an audio output device"). For instance, masking contour curve data, such as PTC or MT, may be used to calculate ratio and threshold parameters for a given frequency subband, while audiogram data may be used to calculate gain within a given frequency subband.

DSP parameters in a processing function may also be calculated by optimizing perceptually relevant information (e.g. perceptual entropy) through parameterization using user xF SM hearing data (see commonly owned U.S. Pat. No. 10,455,335 and pending U.S. application Ser. No. 16/538,541, "Systems and methods for modifying an audio signal using custom psychoacoustic models"). Briefly, in order to optimally parameterize a multiband dynamic processor through perceptually relevant information, an audio sample, or body of audio samples, is first processed by a parameterized multiband dynamics processor and the perceptual entropy of the file is calculated according to user hearing data. After calculation, the multiband dynamic processor is re-parameterized according to a given set of parameter heuristics, derived from optimization, and from this—the audio sample(s) is reprocessed and the PRI calculated. In other words, the multiband dynamics processor is configured to process the audio sample so that it achieves a target PRI value for the particular listener, taking into account the individual listener's hearing profile. To this end, parameterization of the multiband dynamics processor is adapted to increase the PRI of the processed audio sample over the unprocessed audio sample. The parameters of the multiband dynamics processor are determined by an optimization process that uses a specific PRI target as its optimization criteria. In particular, if a measure similar to perceptual entropy is used as the PRI metric, the result of an xF SM test may be used to derive the shape of the spreading function(s) across at least part of the audible range, which represents a central component of a perceptual entropy calculation.

Other parameterization processes commonly known in the art may be used to calculate parameters based off user-generated hearing data. For instance, common prescription techniques for linear and non-linear DSP may be employed. Well known procedures for linear hearing aid algorithms include POGO, NAL, and DSL. See, e.g., H. Dillon, Hearing Aids, 2nd Edition, Boomerang Press, 2012.

Subsequently, the parameters may be stored and/or outputted to a digital signal processing function.

The presented technology offers a more efficient and comprehensive hearing test methodology relative to traditional suprathreshold testing techniques, such as MT or PTC testing. By concurrently sweeping a signal probe and a masker probe at a fixed frequency ratio across the audible spectrum using a cross-frequency simultaneous masking (xF SM) approach, more detailed hearing data may be acquired from a user in a shorter period of time—leading to richer or more accurate test results by mitigating user hearing fatigue. The rich hearing data resulting from this xF SM approach may then be used to calculate parameters for a digital signal processing function—or generally may be used to better assess an underlying hearing impairment.

Methods according to the above-described examples can be implemented using computer-executable instructions that are stored or otherwise available from computer readable media. Such instructions can comprise, for example, instructions and data which cause or otherwise configure a general-purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smartphones, small form factor personal computers, personal digital assistants, rack-mount devices, standalone devices, and so on. Functionality described herein also can be embodied in peripherals or add-in cards. Such functionality can also be implemented on a circuit board among different chips or different processes executing in a single device, by way of further example. The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

What is claimed is:

1. A method for conducting a cross frequency simultaneous masking (xF SM) test, the method comprising:
   generating a signal probe and a masker probe, wherein a center frequency of the signal probe and a center frequency of the masker probe are separated by a first fixed frequency ratio, wherein the first fixed frequency ratio is between 1.0 and 1.5;
   for a given frequency range, generating a first xF SM curve by:
   sweeping the signal probe and the masker probe across the given frequency range while maintaining the first fixed frequency ratio between the signal probe and the masker probe;
   maintaining the masker probe at a pre-determined masker amplitude;
   adjusting the amplitude of the signal probe in response to a series of user inputs; and
   interpolating the series of user inputs to generate the first xF SM curve.

2. The method of claim 1, wherein the first xF SM curve is an xF MT curve, and the method further comprises:
   constructing, based on the xF MT curve, one or more masked threshold curves across a range of audible frequencies, one or more psychophysical tuning curves, or a pure tone threshold audiogram.

3. The method of claim 1, further comprising, for the given frequency range, generating a second xF SM curve by:
   sweeping the signal probe and the masker probe across the given frequency range while maintaining a second fixed frequency ratio between the center frequency of the signal probe and the center frequency of the masker probe;

adjusting the amplitude of the signal probe in response to a second series of user inputs; and interpolating the second series of user inputs to generate the second xF SM curve.

4. The method of claim 3, wherein the second fixed frequency ratio is different than the first fixed frequency ratio.

5. The method of claim 4, further comprising:

interpolating between the first xF SM curve, generated for the first fixed frequency ratio, and the second xF SM curve, generated for the second fixed frequency ratio; and based on the interpolation, constructing one or more masked threshold curves across a range of audible frequencies, one or more psychophysical tuning curves, or a pure tone threshold audiogram.

6. The method of claim 3, wherein the second fixed frequency ratio is the same as the first fixed frequency ratio and the method further comprising:

averaging the first xF SM curve and the second xF SM curve to generate a first averaged xF SM curve for the first fixed frequency ratio.

7. The method of claim 6, further comprising:

for the given frequency range, generating a second averaged xF SM curve for a fixed frequency ratio different than the first fixed frequency ratio;

interpolating between the first averaged xF SM curve and the second averaged xF SM curve; and based on the interpolation, constructing a masked threshold curve, a psychophysical tuning curve, or an audiogram.

8. The method of claim 1, further comprising performing a threshold hearing test or receiving user input to estimate the pre-determined masker amplitudes of the masker probe, wherein the masker is audible to a given listener of the xF SM test.

9. The method of claim 1, wherein adjusting the amplitude of the signal probe in response to the user input comprises:

increasing the amplitude of the signal probe in response to a determination that the user input is received; and decreasing the amplitude of the signal probe in response to a determination that the user input is not received.

10. The method of claim 9, wherein the amplitude of the signal probe is continuously adjusted in response to the series of user inputs.

11. The method of claim 1, further comprising providing the sweeping signal probe and masker probe to a user of an audio output device as an auditory stimulus, wherein the series of user inputs comprises user responses indicating the user's perception of the auditory stimulus.

12. The method of claim 10, wherein the user input comprises user responses obtained in response to a Bekesy testing paradigm.

13. The method of claim 1, wherein the given frequency range comprises at least a portion of the audible spectrum.

14. The method of claim 1, wherein the given frequency range is from 500 Hertz (Hz) to 6 kilohertz (kHz).

15. The method of claim 1, wherein:

the cross frequency simultaneous masking test is a cross frequency masked threshold test;

the signal probe is a tone signal; and the masker probe is a noise signal.

16. The method of claim 1, wherein:

the cross frequency simultaneous masking test is a cross frequency psychophysical tuning test;

the signal probe is a masking signal; and the masker probe is a tone signal.

17. The method of claim 4, wherein:

the first fixed frequency ratio is between 1.0 and 1.5; and the second fixed frequency ratio is different from the first fixed frequency ratio.

18. The method of claim 1, wherein the cross frequency simultaneous masking curve is used to calculate one or more parameters for a processing function.

19. The method of claim 1, wherein sweeping the signal probe and the masker probe across the given frequency range comprises:

sweeping from an intermediate frequency value to a maximum frequency value, the maximum frequency value greater than the intermediate frequency value;

sweeping from the maximum frequency value to a minimum frequency value, the minimum frequency value less than the maximum frequency value and less than the intermediate frequency value; and sweeping from the minimum frequency value to the intermediate frequency value.

* * * * *